United States Patent [19]

Darin et al.

[11] 4,284,523
[45] Aug. 18, 1981

[54] MINIMIZING OXYGENATED AROMATIC COMPOUND CONTENT OF AQUEOUS SOLUTION OF RECLAIMED METAL OXIDATION CATALYST

[75] Inventors: John K. Darin; Walter Partenheimer, both of Naperville, Ill.; Joseph D. Figuly, Munster, Ind.

[73] Assignee: Standard Oil Company (Indiana), Chicago, Ill.

[21] Appl. No.: 152,159

[22] Filed: May 22, 1980

Related U.S. Application Data

[63] Continuation of Ser. No. 968,073, Dec. 11, 1978, abandoned.

[51] Int. Cl.$^3$ .................... B01J 23/94; B01J 23/92; C07C 51/265; C01G 45/00; C01G 51/06
[52] U.S. Cl. .................... 252/420; 252/412; 423/50; 423/140; 562/414; 562/485; 562/486
[58] Field of Search ............... 252/420, 412; 562/414, 562/416, 485, 486; 423/50, 140

[56] References Cited

U.S. PATENT DOCUMENTS

| 3,497,552 | 2/1970 | Olsen | 562/486 |
| 3,873,468 | 3/1975 | Kobinata et al. | 252/412 |

*Primary Examiner*—P. E. Konopka
*Attorney, Agent, or Firm*—Fred R. Ahlers; William H. Magidson; William T. McClain

[57] ABSTRACT

This invention relates to the reclamation of metal oxidation catalysts by water extraction of a high boiling residual mixture remaining after separation of a benzene di- and/or tricarboxylic acid; e.g., the phthalic acids, trimesic acid or trimellitic acid and reaction solvent, if one is used, from the fluid oxidation effluents produced by the catalytic liquid phase oxidation of a xylene, mesitylene, psendocumene or o-xylene and psendocumene with a source of molecular oxygen in the presence or in the absence of a reaction solvent.

5 Claims, No Drawings

MINIMIZING OXYGENATED AROMATIC COMPOUND CONTENT OF AQUEOUS SOLUTION OF RECLAIMED METAL OXIDATION CATALYST

This is a continuation of application Ser. No. 968,073, filed Dec. 11, 1978, now abandoned.

TECHNICAL FIELD

This invention relates to the reclamation of metal oxidation catalysts by water extraction of high boiling residual mixture remaining after separation of a benzene-di- and/or tricarboxylic acid; e.g., the phthalic acids, trimesic acid or trimellitic acid and reaction solvent, if one is used, from the fluid oxidation effluents produced by the catalytic liquid phase oxidation of a xylene, mesitylene, pseudocumene or o-xylene and pseudocumene with a source of molecular oxygen in the presence or in the absence of a reaction solvent. More particularly, this invention pertains to minimizing the oxygenated aromatic compounds content of the aqueous extract solution of the oxidation catalysts metals which are primarily cobalt and manganese but can include cerium by dilution of the extract solution with additional water.

BACKGROUND ART

U.S. Pat. No. 2,964,559; No. 3,557,173; and No. 3,673,154 among other patents disclose reclaiming of oxidation metal catalyst cobalt or cobalt and manganese either from the acetic acid mother liquor or a concentrate thereof after separation of such mother liquor and solid iso- or terephthalic acid precipitate from the suspension of such acids in said mother liquor resulting from the liquid phase oxidation of mixed xylenes or m- or p-xylene with air at an elevated temperature above 100° C. in the presence of acetic acid solution of cobalt or cobalt and manganese, generally as their acetates, at an elevated pressure to maintain at least the acetic acid solvent in the liquid phase.

U.S. Pat. No. 2,964,559 teaches that after separating suspended phthalic acids from acetic acid mother liquor and distilling water and acetic acid from said mother liquor leaving a residue, water extraction of the residue reclaims 93% of the cobalt and 94% of the manganese but also extracts 72 mole percent of the phthalic anhydride as the free acid and 80 to 100% of the nickel, iron and chromium present.

U.S. Pat. No. 3,557,173 is concerned with eliminating o-phthalic acid from the cobalt reclaimed from the acetic acid mother liquor. This is done by dehydrating the acetic acid mother liquor (e.g., by addition of acetic anhydride thereto or by distillation of at least 50% of the acetic acid therefrom) whereby anhydrous cobalt acetate precipitates and is recovered by filtration.

U.S. Pat. No. 3,673,154 is concerned with reclamation of cobalt free of iron and chromium. This is done by distilling acetic acid and water from the mother liquor to a pH above 3 (e.g., pH 3.15 to 4.5) which precipitates iron and chromium, removing the Fe and Cr containing precipitate, adding sodium carbonate to precipitate cobalt carbonate and form a soluble form of nickel. Dissolving cobalt carbonate in acetic acid provides the solvent and metal catalyst for the next oxidation of xylene.

Published Japanese Patent Application No. 14,339/71 also concerned with the rejection of iron group contaminants and oxygen-containing aromatic compounds from reclaimed Co or Co and Mn catalyst metals. This is accomplished by distilling acetic acid from the mother liquor after phthalic acid product separation. The distillation residue is extracted either with water or aqueous alkaline carbonate (e.g. $Na_2CO_3$) solution. The water extract solution is buffered to a pH of 4.5 to precipitate basic iron acetate. The filtrate after removal of the iron acetate precipitate is treated with sodium carbonate to precipitate cobalt and manganese as carbonates. The extraction with aqueous alkaline carbonate leaves a solid residue which, after recovery from the aqueous solution, is dissolved in an inorganic acid. Buffering the acid solution to pH 4–5 with sodium acetate precipitates iron group metals so that after their removal, Co and Mn can be precipitated as carbonates.

British Patent Specification No. 1,413,829 is concerned with the rejection of iron group contaminant corrosion metals from cobalt and manganese reclaimed as their carbonates from residues comprising concentrates derived by distilling acetic acid and water from the acetic acid mother liquor after recovery of suspended iso- or terephthalic acid. Such residues are extracted with water in an amount of from 3 to 5 weight parts per weight part of residue because such amounts of water dissolve at 80° C. 90 to 98% of the cobalt and manganese content of the residue and provide an extract solution (after separating insolubles) of pH 3.5–5.0 which dissolves relatively little of the iron group metals present. High quality cobalt and manganese carbonates can be precipitated from such solution after its pH is adjusted preferably to pH in the range of 7 to 8.1 by the use of sodium carbonate and/or bicarbonate.

Said British Patent also discloses that use of water in weight amount equal to the weight of the residue dissolves at 80° C. only 72 to 81% of Co and 66–76% of Mn in the residue.

The foregoing techniques for reclaiming Co and/or Mn, while satisfactory when applied to residues obtained from the production of iso- or terephthalic acid, on their face appear either not applicable to or not suitable for the reclamation of cobalt and manganese from residues obtained from the production of o-phthalic acid or its coproduction with trimellitic acid by the respective neat oxidation of liquid o-xylene or liquid mixture of o-xylene and pseudocumene. Such prior reclamations of catalyst metals by change of water content or pH of acetic acid mother liquors do not appear to be applicable to the present problem. The other prior catalyst metal reclamations do not appear to be suitable because they must use rather high weight ratios of water to residue (3 to 5:1) to extract 90% or more of the residue's catalyst metals contents and at such water to residue ratios would appear to dissolve excessive quantities of the oxygen-containing aromatic compounds in the residue.

Recently there have been developed catalytic air oxidation processes whereby either o-phthalic acid is produced from liquid o-xylene or a mixture of o-phthalic acid and trimellitic acid is produced from co-oxidation of liquid o-xylene and pseudocumene neat, that is without the use of extraneous reaction solvents or diluents. For example, the processes disclosed in U.S. patent applications Ser. No. 867,050, filed Jan. 5, 1978 and Ser. No. 874,127, filed Feb. 1, 1978. The fluid reaction effluents from such "solventless" processes can contain from 70 to 92 weight percent o-phthalic acid or mixture of o-phthalic and trimellitic acids. Such fluid effluents can be directly processed to dehydrate the acids to their intramolecular anhydrides and to evaporate said anhydride and materials of lower boiling point in a single step at a pressure from 760 mm Hg down to 40 mm Hg and obtain partially purified anhydride products by the partial condensation at a temperature above the dew point of water but below the boiling points of the anhydrides whereby the condensates collected are partially purified anhydride products. Such substantially simultaneous dehydration and evaporation leaves a liquid residue which contains from 50 to 85%, preferably 65 to 85%, of the anhydride (phthalic anhydride when o-xylene alone was oxidized and trimellitic anhydride when both o-xylene and pseudocumene were simultaneously oxidized) which acts as a flux to provide a mixture which is liquid and relatively free flowing at the 180° C. to 235° C. temperatures at which such residues are formed.

We have discovered that relatively small amounts of water, substantially less than the 16 to 17 to 1 water to residue ratios of U.S. Pat. No. 2,964,559 or the 3:1 to 5:1 water to residue ratios of the British Patent, quite surprisingly will at temperatures of 75 to 80° C. extract more than 90 weight percent of the catalyst metals and less than 25% of the o-phthalic acid from the residues left after the above preparation and recovery of partially purified intramolecular anhydride products and retain the catalyst metals as solutes even at temperatures of 23° C. to 24° C. We also found that, although a substantial amount of the oxygen-containing aromatic impurity compounds were also dissolved by the small amount of water, unexpectedly a substantial proportion of the dissolved impurity compounds could be rejected by diluting the extract solution with additional water without substantial change of operating temperature.

STATEMENT OF THE INVENTION

More than 85 weight percent of cobalt and/or manganese and a substantial proportion of cerium can be extracted at temperatures of from 70° C. to 100° C. with water from residues defined below at a water to residue weight ratio of from 0.35:1 up to 1.5:1. The oxygen-containing aromatic impurities co-dissolved by such extraction can be rejected by cooling the extract solution to a temperature of 20° to 35° C. and be even further rejected, preferably by diluting the extract solution with an amount of additional water to precipitate 15 to 20% of the dissolved oxygen-containing aromatic compounds boiling higher than the anhydride of trimellitic acid before separating the extract solution from insolubles and precipitates or, more preferably, diluting with additional water the mixture of extract solution and insolubles at 20° to 25° C. with an amount of additional water equal to 2 to 2.5 times the weight of the extract solution.

The present inventive aqueous extractions can be practiced with residues obtained from the catalytic liquid phase oxidation of m-xylene, p-xylene or mesitylene with air in the presence of acetic acid solution containing a source of bromine ions as well as ions of one or more or all three of cobalt, manganese or cerium after first separating isophthalic, terephthalic or trimesic acid from the fluid effluent and then separating water and acetic acid from the remainder of the reaction mixture.

Other residues to be extracted, and are preferably extracted, according to the present invention are obtained by subjecting to dehydration and evaporation conducted at a temperature of 180° C. to 235° C. and a pressure of 760 mm to 40 mm Hg, the fluid effluent of liquid o-xylene or liquid mixture of o-xylene and pseudocumene oxidized with molecular oxygen in the absence of an extraneous material as reaction solvent or diluent at a temperature in the range of from 150° C. up to 235° C. at a gauge pressure of from 17 up to 30 $kg/cm^2$ and in the presence of from 3 up to 20 weight percent water. By said dehydration and evaporation the o-phthalic acid as o-phthalic and trimellitic acids are converted to their intramolecular anhydrides and such anhydrides and materials boiling below such anhydrides are evaporated. The mixed vapors can be partially condensed to obtain a partially purified phthalic anhydride or partially purified phthalic anhydride mixture with trimellitic anhydride or separate partially purified phthalic anhydride and partially purified trimellitic acid anhydride. The residues left by such dehydration and evaporation contain from 50 up to 85, preferably 65 to 85, weight percent intramolecular anhydride as flux for the materials boiling higher than the intramolecular anhydrides including the organo-metal compounds containing the extractable catalyst metals.

Typical such residues from the preparation of phthalic anhydride from the dehydration and evaporation conducted with fluid effluent from the neat oxidation of liquid o-xylene are shown in TABLE I below

TABLE I

| Component of Residue No. | Residue Compositions | | | |
|---|---|---|---|---|
| | 1 | 2 | 3 | 4 |
| Co, wt. % (as element) | 1.14 | 1.08 | 1.36 | 0.62 |
| Mn, wt. % (as element) | 3.38 | 2.29 | 3.34 | 1.85 |
| Br, wt. % (as element) | 1.32 | 0.90 | 0.78 | 0.87 |
| o-Toluic Acid, wt. % | 0.03 | 0.23 | 0.15 | 0.04 |
| Phthalide, wt. % | 0.01 | 0.20 | 0.18 | 10 ppm |
| 2-Carboxybenzaldehyde, wt. % | 0.77 | 1.00 | 1.03 | 0.41 |
| Benzoic Acid, wt. % | 0.56 | 1.03 | 0.69 | 0.60 |
| $O_2$-Containing Aromatics, wt. % | 20.66 | 15.92 | 26.77 | 11.50 |
| Phthalic Anhydride, wt. % | 72.16 | 77.37 | 65.70 | 84.50 |

Other representative residue compositions will appear in the examples to follow.

The residue can be extracted with water according to the present invention after the residues have been cooled, and solidified and ground. Or the residues can be extracted according to the present invention by quenching the residue with water at ambient pressure in an open vessel or in a closed vessel at from 760 down to 40 mm Hg and from the 180° C. to 235° C. temperature at which the residue is produced down to a temperature of 70° C. to 100° C. using an amount of water which leaves an amount thereof as liquid water equal to the weight of the residue. The excess quench water is of course, converted to steam which, if desired, can be readily withdrawn per se and its content recovered or used in known manner.

The residue from the preparation of phthalic anhydride by the dehydration-evaporation of liquid effluent from the neat air oxidation of o-xylene amounts to from 10 to 12 weight percent of the liquid oxidation effluent even though such residue contains from 50 up to 85 weight percent phthalic anhydride.

In TABLE II to follow there are given the composition of a ground, solidified residue from the dehydration-evaporation of liquid effluent from the neat air oxidation of o-xylene and the results of the extractions of such residue at 24° C. with water at a 1:1 and a 0.35:1 weight ratio of water to residue. The results of such extractions are shown as "Selectivity %" which is the decimal fraction (expressed as %) of the weight of a component extracted divided by the weight of the same component in the residue feed. In the column headings, "W/R" is used to designate Water to Residue weight ratio.

TABLE II

AQUEOUS EXTRACTION AT 24° C. OF RESIDUE FROM DEHYDRATION AND EVAPORATION OF EFFLUENT FROM NEAT OXIDATION OF ORTHO-XYLENE

| Residue Components | Wt. % of Residue | W/R of 1:1 Selectivity % | W/R of 0.35:1 Selectivity % |
|---|---|---|---|
| Benzoic Acid | 4.4 | 78 | 85 |
| Toluic Acid | 0.5 | 80 | 81 |
| Phthalic Anhydride (Acid) | 68.0 | (23) | (19) |
| Iso. and Terephthalic Acid | 1.4 | 62 | 53 |
| Trimellitic Anhydride (Acid) | 3.9 | (92) | (77) |
| Dicarboxynaphthalene | 0.4 | 95 | 75 |
| Methylcarboxybenzophenone | 3.4 | 92 | 72 |
| Tricarboxybenzophenone | 8.1 | 90 | 74 |
| Bis Carboxyanthraquinone | 0.6 | 85 | 75 |
| Bromine[1] | 1.19 | 95 | 85 |
| Cobalt[1] | 0.47 | 99 | 89 |
| Manganese[1] | 0.81 | 95 | 87 |
| Iron[2] | 0.09 | 79 | 75 |
| Chromium[2] | 0.02 | 79 | 69 |
| Sodium[3] | 0.12 | 92 | 89 |

[1]Component of oxidation catalyst reported as element.
[2]Metals of corrosion of apparatus elements.
[3]Contaminant metal from washing of apparatus.

In the above table, the ions (organic or inorganic) associated with the six elements shown have not been taken into account. Thus the sum of the numbers shown in the column headed "Wt. % of Residue" is not 100%. Although the major (68 wt. %) component in the residue extracted was phthalic anhydride, the component in the extract solution was of course o-phthalic acid. In calculating the selectivity of its extraction its equivalents were taken into account.

It will be noted that the 1:1 extraction at 24° C. achieved a high selectivity (95 to 99%) of extraction of oxidation catalyst components but, somewhat disadvantageously, equally high extraction selectivity occurred for high boiling (boiling above phthalic anhydride) impurities and almost as high selectivity of extraction occurred for the mono-, di- and tricarboxybenzene (except o-phthalic acid) impurities. Unfortunately the extraction with water to residue weight ratio of 0.35:1.0 did not substantially minimize selectivity for extracting the oxygen-containing aromatic compounds while retaining the high (87% and above) selectivity for extraction of the components of oxidation catalyst.

The composition of the insoluble portion of residue after making the foregoing aqueous extractions at the water to residue weight ratios of 1:1 and 0.35:1 are shown in TABLE III to follow.

TABLE III

COMPOSITION OF INSOLUBLES AFTER EXTRACTIONS REPORTED IN TABLE II

| Component | Wt. % Components In W/R: 1:1 Insolubles | Wt. % Components In W/R: 0.35:1 Insolubles |
|---|---|---|
| Benzoic Acid | 0.6 | 1.6 |
| o-Toluic Acid | 0.06 | 0.2 |
| Phthalide | 0.04 | 0.14 |
| o-Phthalic Acid | 98 | 86 |
| Iso- and Terephthalic Acid | 0.2 | 0.4 |
| Trimellitic Acid | 0.15 | 0.8 |
| Dicarboxynaphthalene | 0.05 | 0.12 |
| Methyl Dicarboxybenzophenone | 0.09 | 0.4 |
| Tricarboxybenzophenone | 0.37 | 1.6 |
| Bis (Carboxyanthraquinone) | 0.02 | 0.1 |
| Bromine | 0.24 | 0.36 |
| Cobalt | 0.0083 | 0.076 |
| Manganese | 0.014 | 0.13 |
| Iron | 0.21 | 0.096 |
| Chromium | 0.0058 | 0.0063 |
| Sodium | 0.0031 | 0.0039 |

The foregoing compositions of the insolubles have a higher quality than the feed composition used in the dehydration-evaporation producing the residues extracted because the insolubles have a much lower content of the oxygen-containing aromatics boiling higher than phthalic anhydride.

BEST MODES OF PRACTICING PRESENT INVENTION

EXAMPLE 1

Since extraction with lower weight ratio of water to residue did not achieve the results desired, samples of a residue from a different dehydration-evaporation of a liquid effluent from the neat oxidation of o-xylene were each extracted at 77° C. with a water to residue ratio of 1:1. After such extraction of one sample the slurry was cooled to 24° C. and filtered. The filtrate and filter cake were analyzed. The results are shown in TABLE IV.

TABLE IV

EXTRACTION AT 77° C., FILTRATION AT 24° C. WITH WATER TO RESIDUE WEIGHT RATIO OF 1:1 USING RESIDUE FROM DEHYDRATION-EVAPORATION OF FLUID EFFLUENT FROM NEAT OXIDATION OF ORTHO-XYLENE

| Residue Components | Wt. % of Residue | Component in Filtrate Wt. % | Component in Filtrate Wt. % from Residue |
|---|---|---|---|
| Benzoic Acid | 1.8 | 0.2 | 29 |
| o-Toluic Acid | 0.1 | 0.003 | 8 |
| Phthalide | 0.3 | 0.05 | 43 |
| Phthalic Anhydride (Acid) | 57.3 | 7.2 | 33 |
| Iso- and Terephthalic Acid | 0.9 | 0.2 | 59 |
| Trimellitic Anhydride (Acid) | 4.0 | 1.5 | 100 |
| Other High Boilers[1] | 17.8 | 7.6 | 113 |
| Bromine | 1.01[2] | 0.31[2] | 81 |
| Cobalt | 0.58 | 0.24 | 110 |
| Manganese | 1.13 | 0.5 | 117 |
| Iron | 0.036 | 0.013[2] | 99 |
| Chromium | 0.011 | 0.004[2] | 95 |
| Nickel | 0.007 | 0.004[2] | 150 |
| Sodium | 0.093 | 0.045 | 128 |

[1]Compounds boiling higher than trimellitic anhydride including dicarboxynaphthalene, methyl dicarboxybenzophenone, tricarboxybenzophenone, and bis(carboxyanthraquinone).
[2]Analysis by X-ray fluorescence; all other elements by atomic absorption.

| Residue Components | Component in Filter Cake Wt. % | Component in Filter Cake Wt. % from Residue |
|---|---|---|
| Benzoic Acid | 2.7 | 70 |
| o-Toluic Acid | 0.1 | 50 |
| Phthalide | 0.1 | 17 |

TABLE IV-continued

EXTRACTION AT 77° C., FILTRATION AT 24° C. WITH WATER TO RESIDUE WEIGHT RATIO OF 1:1 USING RESIDUE FROM DEHYDRATION-EVAPORATION OF FLUID EFFLUENT FROM NEAT OXIDATION OF ORTHO-XYLENE

| | | |
|---|---|---|
| Phthalic Anhydride (Acid) | (76.2) | 62 |
| Iso- and Terephthalic Acid | 1.0 | 51 |
| Trimellitic Anhydride (Acid) | 1.0 | 11 |
| Other High Boilers[1] | 6.4 | 16 |
| Bromine | 0.60[1] | 28 |
| Cobalt | 0.043 | 4 |
| Manganese | 0.053 | 2 |
| Iron | 0.022 | 28 |
| Chromium | 0.0019 | 8 |
| Nickel | 0.0023 | 20 |
| Sodium | 0.0082 | 41 |

[1]Compounds boiling higher than trimellitic anhydride.
[2]Analysis by X-ray fluorescence; all other elements by atomic absorption.

Quite unexpectedly extraction with a water to residue weight ratio of 1:1 at a temperature of 77° C. and then cooling the resulting slurry (extract solution and undissolved solids) to a temperature of 24° C. and filtering at said temperature did effect a decrease in amount of the oxygen containing aromatic compounds dissolved at 24° C. with the same 1:1 weight ratio of water to residue. But equally as surprising was the fact that extraction at 77° C., cooling to 24° C. and filtering at 24° C. did not decrease the selectivity of catalyst components remaining in the cooled extract solution.

The original purpose for diluting the extract solution was to provide more solvent for greater dilution of the high boilers and retain them in solution when precipitating the metal oxidation catalysts as their carbonates. But instead of further diluting the concentration of the high boiler's concentration in the solution, a high proportion of the high boilers, quite unexpectedly were precipitated as TABLE V indicates and TABLE VII demonstrates.

A second sample of residue (composition shown in TABLE IV) is extracted with 1:1 water to residue weight ratio at a temperature of 77° C. The resulting slurry of undissolved solids in aqueous extract solution is filtered at 24° C. and the filtrate is diluted with two weight parts of water per weight part of filtrate and a final temperature of 21° C. Upon dilution of the 24° C. filtrate, quite surprisingly a precipitate formed. The diluted (21° C.) filtrate is separated from the 21° C. precipitate and said precipitate is analyzed. The 21° C. precipitate has the composition shown in TABLE V.

TABLE V

COMPOSITION OF PRECIPITATE FORMED BY WATER DILUTION AT 2:1 OF 24° C. FILTRATE FROM 77° C. EXTRACTION AT 1:1 WATER TO RESIDUE RATIO

| | Wt. % of Component | |
|---|---|---|
| Components | In 21° C. Precipitate | From Residue |
| Benzoic Acid | 0.8 | 4.2 |
| o-Toluic Acid | 0.01 | 1.0 |
| Phthalide | 0.4 | 1.3 |
| Phthalic Acid | 7.5 | 1.3 |
| Iso- and Terephthalic Acid | 0.6 | 6.3 |
| Trimellitic Acid | 2.1 | 5.0 |
| Other High Boilers[1] | 29.9 | 16.1 |
| Bromine | 1.79 | 17 |
| Cobalt | 0.367 | 6 |
| Manganese | 0.68 | 6 |
| Iron | 0.11 | 29 |
| Chromium | 0.048 | 42 |

TABLE V-continued

COMPOSITION OF PRECIPITATE FORMED BY WATER DILUTION AT 2:1 OF 24° C. FILTRATE FROM 77° C. EXTRACTION AT 1:1 WATER TO RESIDUE RATIO

| | Wt. % of Component | |
|---|---|---|
| Components | In 21° C. Precipitate | From Residue |
| Nickel | 0.0046 | 6 |
| Sodium | 0.033 | 34 |

[1]Compounds boiling higher than trimellitic anhydride.
[2]Analysis by X-ray fluorescence; all other elements by atomic absorption.

EXAMPLE 2

In this example the third sample of residue (composition shown in TABLE IV) is extracted at 77° C. with water to residue weight ratio of 1:1 and, without cooling and separating the resulting slurry, it is diluted with water in the weight ratio of water to solution portion of the slurry of 2.5:1. Additional precipitation was observed during such dilution. The diluted slurry's final temperature is 21° C. so it is warmed to 24° C. and then filtered. The filter cake is analyzed and is found to have the composition shown in TABLE VI.

TABLE VI

RESIDUE EXTRACTION AT 77° C. WITH 1:1 WATER TO RESIDUE AND RESULTANT SLURRY DILUTED WITH 2:1 WATER TO EXTRACT SOLUTION PORTION OF SLURRY

| | Wt. % Component | |
|---|---|---|
| Component | In 24° C. Filter Cake | From Residue |
| Benzoic Acid | 1.6 | 52 |
| o-Toluic Acid | 0.04 | 23 |
| Phthalide | 0.12 | 23 |
| Phthalic Acid | 65.6 | 76 |
| Iso- and Terephthalic Acid | 0.8 | 52 |
| Trimellitic Acid | 1.1 | 16 |
| Other High Boilers[1] | 9.9 | 32.4 |
| Bromine[2] | 0.87 | 50 |
| Cobalt | 0.079 | 8 |
| Manganese | 0.139 | 7 |
| Iron | 0.039 | 63 |
| Chromium | 0.015 | 80 |
| Nickel | 0.0036 | 30 |
| Sodium | 0.0068 | 4 |

[1]Compounds boiling higher than trimellitic anhydride.
[2]Bromine determined by X-ray fluorescence; all other by atomic absorption.

It was noted that the above 24° C. Filter Cake weight was substantially equal to the sum of the weights of the 21° C. precipitate and the insolubles left behind by the 77° C. extraction in Example 1. However, the 24° C. Filter Cake contained more bromine, iso- and terephthalic acid and other high boilers than the total thereof in the 77° C. insolubles and the 21° C. precipitate from Example 1. Hence, the solution separated from the 24° C. Filter Cake (diluted extract solution) contains less of the high boilers than would be expected either from the results of Example 1 or from an extraction of the same residue with a water to residue weight ratio of 3:1.

The first step in the present inventive process is the leaching of the before defined residue with water. Such first step has been a part of the prior art technique for recovery of metal oxidation catalysts in said residues. Since the metal oxidation catalysts are, after residue leaching, dissolved in the aqueous extract solution together with some of the oxygen-containing aromatic by-products, the catalyst metals are generally precipitated from the extract solution as carbonates and then converted to their carboxylates (e.g. acetates, naphthenates, and the like) soluble in the reaction medium or in the di- or trimethyl benzene to be oxidized.

In TABLE VII to follow there are given the composition of the residue before extraction, the composition of the solids left (First Solids) after water extraction, the composition of the solids precipitated and recovered after dilution of the separated extract solution and the composition of the carbonate precipitate of the catalyst metal. Said residue, First Solids and Second Solids are from the process of Example 1.

TABLE VII

| Residue as feed: Component | Wt. % | Wt. % Component In: | | |
|---|---|---|---|---|
| | | First Solids | Second Solids | Carbonate Precipitate |
| Bromine | 1.01 | 0.588 | 1.79 | 0.16 |
| Cobalt | 0.58 | 0.075 | 0.367 | 14.0 |
| Manganese | 1.13 | 0.098 | 0.68 | 25.3 |
| Iron | 0.036 | 0.021 | 0.11 | 0.41 |
| Chromium | 0.011 | 0.004 | 0.048 | 0.031 |
| Nickel | 0.007 | 0.003 | 0.004 | 0.14 |
| Sodium | 0.093 | 0.011 | 0.033 | 0.52 |
| Benzoic Acid | 1.8 | 2.7 | 0.8 | ND[2] |
| o-Toluic Acid | 0.1 | 0.1 | 0.01 | ND |
| Phthalide | 0.3 | 0.1 | 0.4 | ND |
| o-Phthalic Acid | 57.3 | 76.2 | 7.5 | 0.35 |
| IA/TA[1] | 0.9 | 1.0 | 10.6 | 0.01 |
| Trimellitic Acid | 4.0 | 1.0 | 2.1 | 0.12 |
| High Boilers | 17.8 | 6.4 | 29.9 | 0.70 |

[1] IA/TA is isophthalic acid and terephthalic acid.
[2] "ND" is none detected; i.e., amount present below detectability by analytical procedure used.

In TABLE VIII to follow there are given the composition of the residue before extraction, the composition of the solids composite from dilution of the slurry formed by water extraction of the residue according to Example 2, and the composition of catalyst metal carbonate precipitate.

TABLE VIII

| Residue as feed: Component | Wt. % | Wt. % Component In: | |
|---|---|---|---|
| | | Solids From Slurry Dilution | Carbonate Precipitate |
| Bromine | 1.01 | 0.87 | 0.12 |
| Cobalt | 0.58 | 0.079 | 12.1 |
| Manganese | 1.13 | 0.138 | 24.5 |
| Iron | 0.036 | 0.039 | 0.44 |
| Chromium | 0.011 | 0.015 | 0.036 |
| Nickel | 0.007 | 0.0036 | 0.12 |
| Sodium | 0.093 | 0.0068 | 0.56 |
| Benzoic Acid | 1.8 | 1.6 | ND |
| o-Toluic Acid | 0.1 | 0.04 | ND |
| Phthalide | 0.3 | 0.12 | ND |
| o-Phthalic Acid | 57.3 | 65.6 | 0.40 |
| IA/TA* | 0.9 | 0.8 | 0.05 |
| Trimellitic Acid | 4.0 | 1.1 | ND |
| High Boilers | 17.8 | 9.9 | 0.49 |

*Iso- and terephthalic acids

In TABLE IX to follow there is given the composition of the carbonate precipitate of metal catalyst obtained by such precipitation from the extract solution separated from the slurry formed after leaching the residue with water in the weight ratio of water to residue of 1:1. It will be noted that a major proportion of the carbonate precipitate is High Boiler Compounds. Such High Boiler compounds would dissolve if the carbonate precipitate would be taken up in active acid to obtain the metals cobalt and manganese as their acetates.

TABLE IX

| Residue Leached: Component | Wt. % | Wt. % Components In Carbonate Precipitate |
|---|---|---|
| Bromine | 1.01 | 13.48 |
| Cobalt | 0.58 | 8.24 |
| Manganese | 1.13 | 16.78 |
| Iron | 0.036 | 0.33 |
| Chromium | 0.011 | 0.08 |
| Nickel | 0.007 | 0.09 |
| Sodium | 0.093 | 0.20 |
| Benzoic Acid | 1.8 | 0.05 |
| o-Toluic Acid | 0.1 | 0.001 |
| Phthalide | 0.3 | 0.19 |
| o-Phthalic Acid | 57.3 | 0.58 |
| IA/TA* | 0.9 | 0.04 |
| Trimellitic Acid | 4.0 | 0.61 |
| High Boilers | 17.8 | 59.39 |

*Iso- and Terephthalic acids

The processes of Example 1 and Example 2 lead to the recovery of catalyst metals (Co and Mn) in their respective percentages of their amounts in the residue of 99% of the cobalt and 92% of the manganese; 92% of the cobalt and 95% of the manganese.

The foregoing techniques applied to water extraction of residue from the dehydration of oxidation effluent containing trimellitic acid or o-phthalic acid and trimellitic acid will provide substantially equivalent results with respect to the reclamation of catalyst metals cobalt and manganese as well as the reclamation of a substantial proportion of cerium when it is used in combination with cobalt, manganese and bromine.

The invention claimed is:

1. The method of reclaiming catalyst metals comprising cobalt and manganese from the residue obtained after separation of benzene di- and/or tricarboxylic acid from the liquid effluent obtained by the liquid phase oxidation of a xylene or a trimethylbenzene and after the evaporation of low boiling materials from the liquid following such separation, or after separation of o-phthalic acid or o-phthalic acid and trimellitic acid after their conversion to their respective intramolecular anhydrides and evaporation of such anhydrides and materials of lower boiling temperature from liquid effluents obtained by the liquid phase oxidation of o-xylene, or a combination of o-xylene and pseudocumene; which catalyst metal reclamation method comprises extracting such residue with water in a weight ratio of water to residue of from 0.35:1 up to 1.5:1 at a temperature in the range of from 70° to 100° C., then diluting the 70° to 100° C. temperature extract solution with water in an amount to precipitate 15 to 20% of the dissolved oxygen-containing compounds boiling higher than the anhydride of trimellitic acid before separating the solids insoluble from said extraction and thereafter cooling the resultant mixture of insolubles, precipitate and diluted extract solution to a temperature in the range of 20° C. to 35° C., or after said 70° C. to 100° C. extraction cooling the resultant mixture of insolubles and aqueous extract solution to a temperature in the range of 20° C. to 35° C. and then diluting the cooled extract solution with an amount of water to precipitate 15 to 20% of the dissolved oxygen-containing compounds boiling higher than the anhydride of trimellitic acid without by said dilution of the cooled solution causing a substantial temperature change from the cooling, and finally separating the solution containing catalyst metal from the insolubles and precipitates.

2. The metal of claim 1 wherein such residue so extracted is obtained from the dehydration and evaporation of liquid effluent from the neat oxidation of liquid o-xylene in the presence of catalysis provided by cobalt and manganese as metal oxidation catalysts promoted by bromine.

3. The method of claim 2 wherein the extraction is conducted at 77° C. with a water to residue weight ratio of 1:1 and the cooling and separating are conducted at a temperature of 21° to 24° C.

4. The method of claim 3 wherein the mixture of extract solution and insolubles is diluted with additional water in an amount of from 2.1 to 2.5 times the weight of extract solution, the resulting diluted mixture is cooled to and filtered at 24° C.

5. The method of claim 3 wherein the mixture of aqueous extract solution and insolubles formed at 77° C. is cooled to 24° C., filtered and the filtrate diluted with an amount of water twice the weight of the filtrate portion of said mixture and the diluted filtrate is then recovered at a temperature of 21° C.

* * * * *

UNITED STATES PATENT OFFICE
CERTIFICATE OF CORRECTION

Patent No. 4,284,523  Dated August 18, 1981

Inventor(s) John K. Darin, Walter Partenheimer, Joseph D. Figuly

It is certified that error appears in the above-identified patent and that said Letters Patent are hereby corrected as shown below:

Patent reads:

| Col. | Line | |
|---|---|---|
| Abstract | 8 | "psendocumene" should be -- pseudocumene -- |
| 1 | 13-14 | "benzene-di-" should be -- benzene di- -- |
| 3 | 10 | "leaves" should be -- leave -- |
| 4 | 57 | "its content" should be -- its heat content -- |
| 5 (Table II) | 20 | "Iso. and" should be -- Iso- and -- |
| 11 | 1 | "The metal" should be -- The method -- |

Signed and Sealed this

Twelfth Day of January 1982

[SEAL]

Attest:

GERALD J. MOSSINGHOFF

Attesting Officer   Commissioner of Patents and Trademarks